(12) United States Patent
Wang et al.

(10) Patent No.: US 7,985,763 B2
(45) Date of Patent: Jul. 26, 2011

(54) HEPATITIS C VIRUS INHIBITORS

(75) Inventors: Li-Wen Wang, Kaohsiung (TW); Tsu-An Hsu, Taipei (TW); Yen-Chun Lee, Taitung (TW); Iou-Jiun Kang, Wandan Township (TW); Chung-Chi Lee, Chung-He (TW); Yu-Sheng Chao, Warren, NJ (US); Jyh-Haur Chern, Taipei (TW)

(73) Assignee: National Health Research Institutes, Miaoli County (TW)

( * ) Notice: Subject to any disclaimer, the term of this patent is extended or adjusted under 35 U.S.C. 154(b) by 98 days.

(21) Appl. No.: 12/055,554

(22) Filed: Mar. 26, 2008

(65) Prior Publication Data

US 2008/0255189 A1    Oct. 16, 2008

Related U.S. Application Data

(60) Provisional application No. 60/910,892, filed on Apr. 10, 2007.

(51) Int. Cl.
A61K 31/404 (2006.01)
C07D 209/08 (2006.01)
(52) U.S. Cl. ......... 514/414; 514/415; 548/465; 548/491
(58) Field of Classification Search .................. 548/465, 548/491; 514/414, 415
See application file for complete search history.

(56) References Cited

U.S. PATENT DOCUMENTS

| | | | |
|---|---|---|---|
| 3,890,348 A * | 6/1975 | Kathawala | 548/491 |
| 4,221,817 A | 9/1980 | Tenne | |
| 4,413,006 A | 11/1983 | Kanno et al. | |
| 4,574,124 A * | 3/1986 | Kabbe et al. | 514/230.5 |
| 5,932,742 A * | 8/1999 | Yoon et al. | 548/312.1 |
| 6,696,487 B2 | 2/2004 | Gerusz et al. | |
| 6,706,751 B2 * | 3/2004 | Aebi et al. | 514/415 |
| 7,094,807 B2 | 8/2006 | Chen et al. | |
| 7,102,007 B2 | 9/2006 | Aebi et al. | |
| 2005/0020624 A1 * | 1/2005 | Aebi et al. | 514/311 |
| 2005/0032849 A1 | 2/2005 | Phadke et al. | |
| 2005/0228013 A1 | 10/2005 | Thurkauf et al. | |
| 2006/0025416 A1 | 2/2006 | Phadke et al. | |
| 2009/0264404 A1 | 10/2009 | Yamashita et al. | |

FOREIGN PATENT DOCUMENTS

| | | |
|---|---|---|
| DE | 2040438 | 3/1971 |
| FR | 2447378 | 1/1979 |
| GB | 1332008 | 10/1973 |
| GB | 2056968 | 3/1981 |
| JP | 2005330284 | 2/2005 |
| JP | 2005/144790 | 5/2005 |
| WO | WO 99/40088 | 8/1999 |
| WO | WO2004/046095 | 6/2004 |
| WO | WO2004/096210 | 11/2004 |
| WO | WO2005/095345 | 10/2005 |
| WO | WO2006/122011 | 11/2006 |

OTHER PUBLICATIONS

Document No. 142:56122, retrieved from CAPLUS on Jan. 6, 2010.*
Document No. 140:209908, retrieved from CAPLUS on Jan. 6, 2010.*
Document No. 86:55235, retrieved from CAPLUS on Jan. 6, 2010.*
Document No. 140:406359, retrieved from CAPLUS on Jan. 6, 2010.*
Document No. 143:163157, retrieved from CAPLUS on Jan. 6, 2010.*
Document No. 139:69296, retrieved from CAPLUS on Jan. 6, 2010.*
Document No. 132:279477, retrieved from CAPLUS on Jan. 6, 2010.*
Jefferson, et al., Bioorg. Med. Chem. Lett., 14, 2004, 5139-5143.*
RN 500201-34-3 , entered in STN Mar. 21, 2003 retrieved from Registry.*
Gugliamelli, Luis et al., Males de la Asociacion Quimica Argentina (1927), 15, pp. 337-362.
Arafa, Reem et al., J. Med. Chem. 2005, 48, 5480-5488.
Cory et al., "Use of an Aqueous Soluble Tetrazolium/Formazan Assay for Cell Growth Assays in Culture," *Cancer Communications*, vol. 3, No. 7, (1991).
Honda et al., Chem. Abst. 135 357776 (2001).
Willson et al. Chem. Abst. 118: 212577 (1993).
Bennett et al., J. Am Chem Soc. 1953 75(23); 6039-6040.

* cited by examiner

*Primary Examiner* — Shawquia Young
(74) *Attorney, Agent, or Firm* — Occhiuti Rohlicek & Tsao LLP

(57) ABSTRACT

A compound of the following formula:

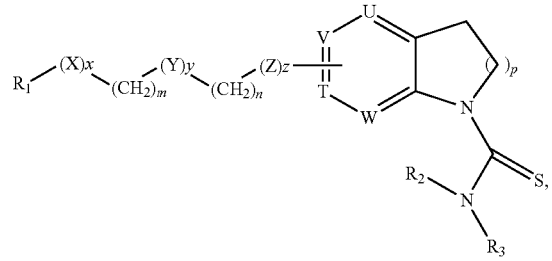

in which $R_1$, $R_2$, $R_3$, U, V, T, W, X, Y, Z, m, n, p, x, y, and z are as defined herein. Also disclosed are (1) a pharmaceutical composition containing such a compound, and (2) a method for treating Hepatitis C virus infection using such a compound.

13 Claims, No Drawings

HEPATITIS C VIRUS INHIBITORS

CROSS REFERENCE TO RELATED APPLICATIONS

This application claims priority to U.S. Provisional Application Ser. No. 60/910,892, filed Apr. 10, 2007. The contents of the prior application are hereby incorporated by reference in their entireties.

BACKGROUND

Hepatitis C virus (HCV) infection is estimated to affect 170 million individuals worldwide. This disease is primarily transmitted through contaminated blood products. Although its spread has been slowed as a result of improvements in blood screening in many countries, it remains the leading cause of liver disease-related deaths in the world. For example, it results in up to 10,000 deaths annually in the U.S. alone. In the absence of new antiviral therapies to combat this disease, the death rate is expected to triple over the next 2 decades.

Current treatments based on interferon-alpha have low success rates, particularly for genotype-1 infections that predominate in Europe, Japan, and the U.S. Also, they are expensive and poorly received by patients. Thus, there is a need to develop better therapeutic agents for treating HCV infection.

SUMMARY

This invention is based on the discovery that certain thiourea compounds are effective in treating hepatitis C virus infection.

In one aspect, this invention relates to a compound having the following formula:

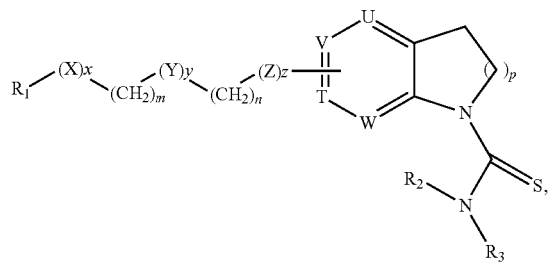

in which each of $R_1$, $R_2$, and $R_3$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl or C(O)R', in which R' is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; each of X, Y, and Z, independently, is O, N($R_a$), S, $C_1$-$C_{10}$ alkylene, $C_2$-$C_{10}$ alkenylene, $C_2$-$C_{10}$ alkynylene, $C_3$-$C_{20}$ cycloalkylene, $C_3$-$C_{20}$ heterocycloalkylene, arylene, heteroarylene, —C(O)—, —C(O)O—, —C(O)N$R_a$—, —N$R_a$C(O)N$R_b$—, —N$R_a$C(S)N$R_b$—, —N$R_a$C(O)O—, —SO$_2$—, or —SO$_2$N$R_a$—, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; each of U, V, T, and W, independently, is N or CR', in which R' is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, O, or N($R_a R_b$), in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl;

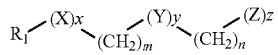

is attached to U, V, or T; each of m and n can be 0, 1, 2, 3, 4, 5, 6, or 7; p is 1 or 2; and each of x, y, and z, independently, is 0 or 1.

Referring to the above-described compounds, a subset can have one or more of the following features: $R_1$ is aryl or heteroaryl; $R_3$ is C(O)R'; and p is 1 or 2. This subset of the compounds may further feature that x and z are 1, Y is 0, and X and Z are 0; x and y are 0, and z is 1, and Z is O; or all x, y, and z are 0.

In another aspect, this invention relates to a compound of the same formula shown above, in which each of $R_1$, $R_2$, and $R_3$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl. Each of X, Y, and Z, independently, is O, N($R_a$), S, $C_1$-$C_{10}$ alkylene, $C_2$-$C_{10}$ alkenylene, $C_2$-$C_{10}$ alkynylene, $C_3$-$C_{20}$ cycloalkylene, $C_3$-$C_{20}$ heterocycloalkylene, arylene, heteroarylene, —C(O)—, —C(O)O—, —C(O)N$R_a$—, —N$R_a$C(O)N$R_b$—, —N$R_a$C(S)N$R_b$—, —N$R_a$C(O)O—, —SO$_2$—, or —SO$_2$N$R_a$—, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; each of U, V, T, and W, independently, is N or CR', in which R' is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, O, or N($R_a R_b$), in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl;

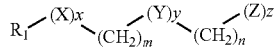

is attached to U or V; each of m and n is 0, 1, 2, 3, 4, 5, 6, or 7; p is 1 or 2; and each of x, y, and z, independently, is 0 or 1.

Referring to the just-described compounds, a subset may have one or more of the following features: $R_3$ is H; $R_1$ is aryl or heteroaryl; p is 1. This subset of the compounds may further feature that x and z are 1, y is 0, and both X and Z are 0; or all x, y, and z are all 0 and both m and n are 0.

The term "alkyl" refers to a monovalent straight or branched hydrocarbon, containing 1-10 carbon atoms. Examples of alkyl include, but are not limited to, methyl, ethyl, n-propyl, i-propyl, n-butyl, i-butyl, and t-butyl. The term "alkylene" refers to a bivalent straight or branched hydrocarbon, containing 1-10 carbon atoms. Examples of alkylene include, but are not limited to, methylene, ethylene, and propylene. The term "alkenyl" refers to a monovalent straight or branched hydrocarbon containing 2-10 carbon atoms and one or more double bonds. Examples of alkenyl, but are not limited to, include ethenyl, propenyl, allyl, and 1,4-butadienyl. The term "alkenylene" refers to a bivalent straight or branched hydrocarbon containing 2-10 carbon atoms and one or more double bonds. The term "alkynyl" refers to a monovalent straight or branched hydrocarbon containing 2-10 carbon atoms and one or more triple bonds. Examples of alkynyl include, but are not limited to, ethynyl, 1-propynyl, 1- and 2-butynyl, and 1-methyl-2-butynyl. The term "alkynylene" refers to a bivalent straight or branched hydrocarbon containing 2-10 carbon atoms and one or more triple bonds. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

The term "cycloalkyl" refers to a monovalent saturated hydrocarbon ring system having 3 to 12 carbon atoms. Examples of cycloalkyl include, but are not limited to, cyclopropyl, cyclobutyl, cyclopentyl, cyclopentenyl, cyclohexyl, cyclohexenyl, cycloheptyl, and cyclooctyl. The term "cycloalkylene" refers to a bivalent saturated hydrocarbon ring system having 3 to 12 carbon atoms. The term "cycloalkenyl" refers to a monovalent non-aromatic hydrocarbon ring system having 3 to 12 carbons and one or more double bonds. Examples include cyclopentanyl, cyclohexanyl, and cycloheptanyl. The term "cycloalkenylene" refers to a bivalent non-aromatic hydrocarbon ring system having 3 to 12 carbons and one or more double bonds. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocyclyl groups include, but are not limited to, piperazinyl, pyrrolidinyl, dioxanyl, morpholinyl, and tetrahydrofuranyl. The term "heterocycloalkylene" refers to a bivalent nonaromatic 5-8 membered monocyclic, 8-12 membered bicyclic, or 11-14 membered tricyclic ring system having one or more heteroatoms (such as O, N, S, or Se). The term "heterocycloalkenyl" refers to a nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkylene, alkenyl, alkenylene, alkynyl, alkynylene, cycloalkyl, cycloalkylene, heterocycloalkyl, heterocycloalkylene, cycloalkenyl, heterocycloalkenyl, aryl, arylene, heteroaryl, and heteroarylene mentioned above include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl.

Shown in the table below are 40 exemplary compounds of this invention:

| Compound No. | Structure | Name |
|---|---|---|
| 1 | 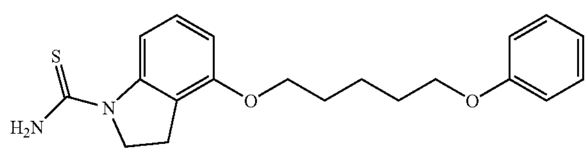 | 4-(5-Phenoxy-pentyloxy)-2,3-dihydro-indole-1-carbothioic acid amide |
| 2 | 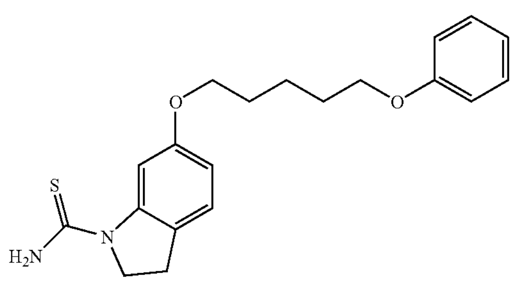 | 6-(5-Phenoxy-pentyloxy)-2,3-dihydro-indole-1-carbothioic acid amide |
| 3 | 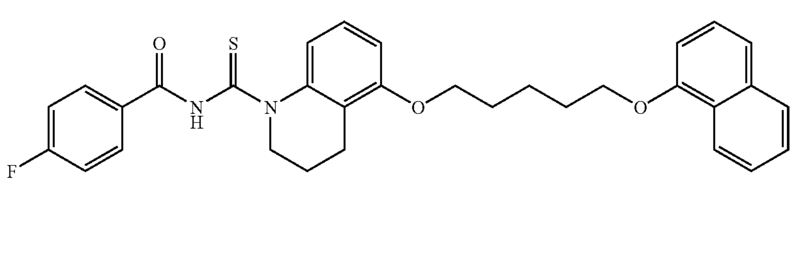 | 4-Fluoro-N-{5-[5-(naphthalen-1-yloxy)-pentyloxy]-3,4-dihydro-2H-quinolin-1-carbothioyl}-benzamide |

| Compound No. | Structure | Name |
|---|---|---|
| 4 | 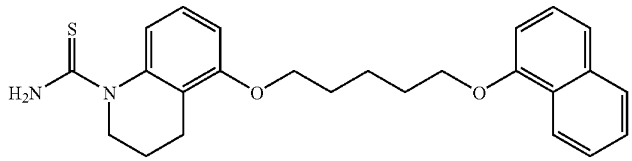 | 5-[5-Naphthalen-1-yloxy)-pentyloxy]-3,4-dihydro-2H-quinolin-1-carbothioic acid amide |
| 5 | 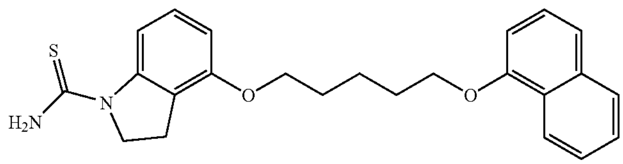 | 4-[5-(Naphthalen-1-yloxy)-pentyloxy]-2,3-dihydro-indole-1-carbothioic acid amide |
| 6 | 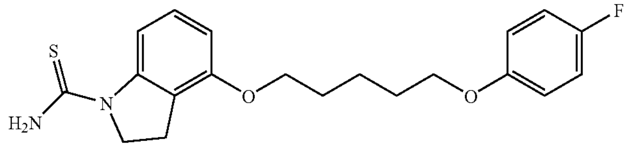 | 4-[5-(4-Fluoro-phenoxy)-pentyloxy]-2,3-dihydro-indole-1-carbothioic acid amide |
| 7 | 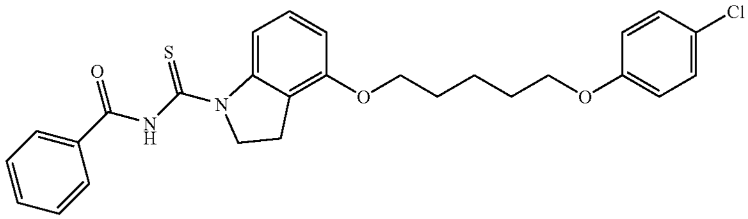 | N-{4-[5-(4-Chloro-phenoxy)-pentyloxy]-2,3-dihydro-indole-1-carbothioyl}benzamide |
| 8 | 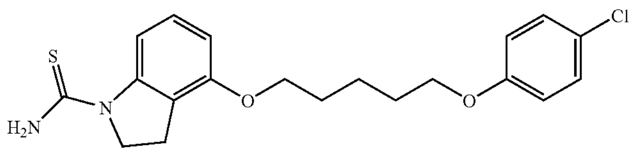 | 4-[5-(4-Chloro-phenoxy)-pentyloxy]-2,3-dihydro-indole-1-carbothioic acid amide |
| 9 | 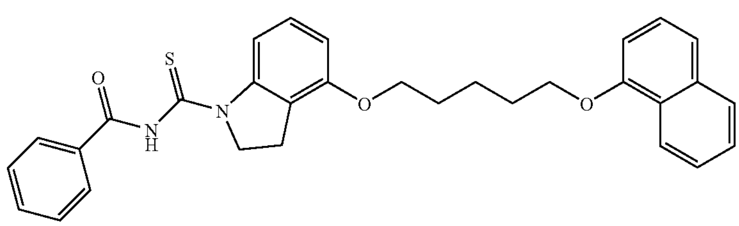 | N-{4-[5-(Naphthalen-1-yloxy)-pentyloxy]-2,3-dihydro-indole-1-carbothioyl}-benzamide |
| 10 | 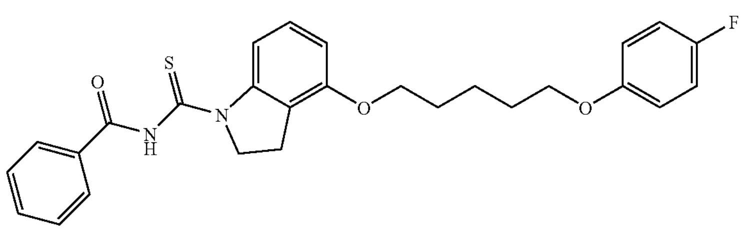 | N-{4-[5-(4-Fluoro-phenoxy)-pentyloxy]-2,3-dihydro-indole-1-carbothioyl}benzamide |

-continued

| Compound No. | Structure | Name |
|---|---|---|
| 11 | 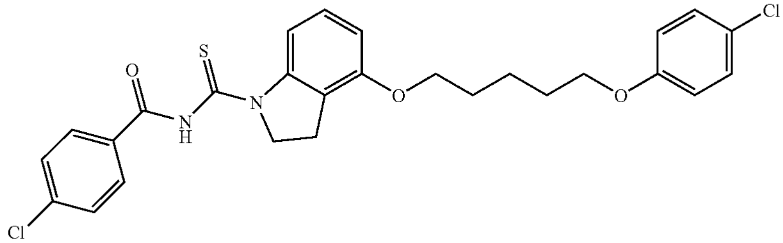 | 4-Chloro-N-{4-[5-(4-chloro-phenoxy)-pentyloxy]-2,3-dihydro-indole-1-carbothioyl}benzamide |
| 12 | 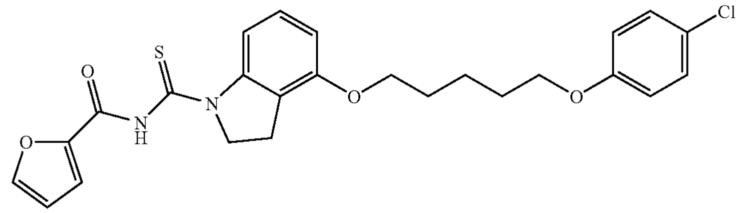 | Furan-2-carboxylic acid {4-[5-(4-chloro-phenoxy)-pentyloxy]-2,3-dihydro-indole-1-carbothioyl}amide |
| 13 | 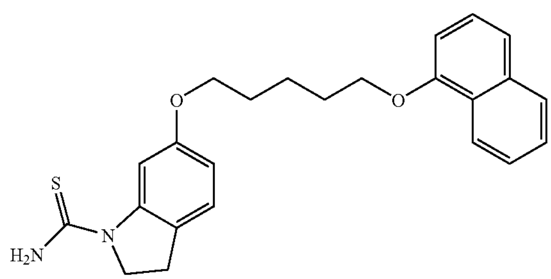 | 6-[5-(Naphthalen-1-yloxy)-pentyloxy]-2,3-dihydro-indole-1-carbothioic acid amide |
| 14 | 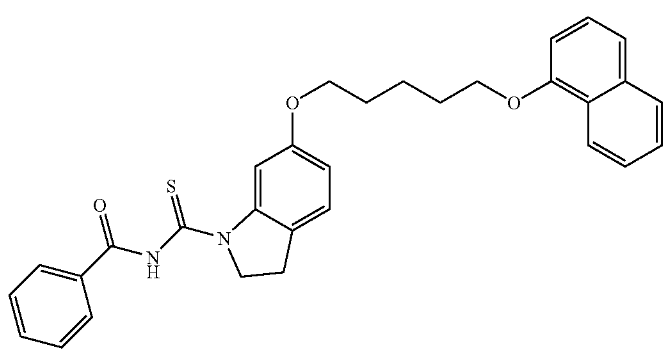 | N-{6-[5-(Naphthalen-1-yloxy)-pentyloxy]-2,3-dihydro-indole-1-carbothioyl}benzamide |
| 15 | 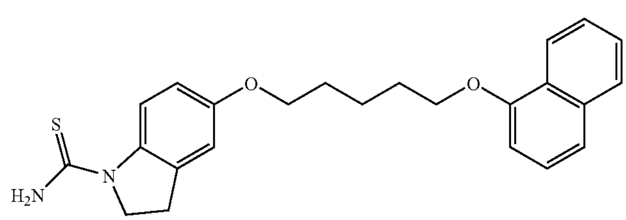 | 5-[5-(Naphthalen-1-yloxy)-pentyloxy]-2,3-dihydro-indole-1-carbothioic acid amide |

-continued

| Compound No. | Structure | Name |
|---|---|---|
| 16 | 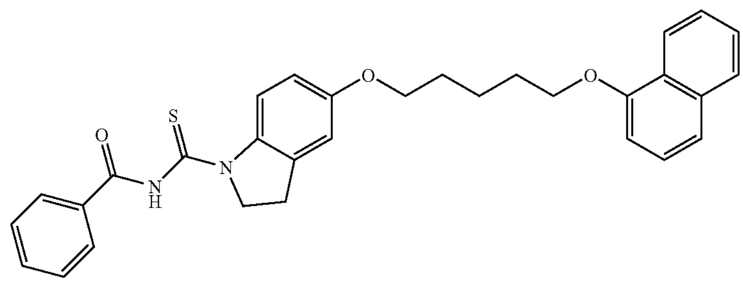 | N-{5-[5-(Naphthalen-1-yloxy)-pentyloxy]-2,3-dihydro-indole-1-carbothioyl}benzamide |
| 17 | 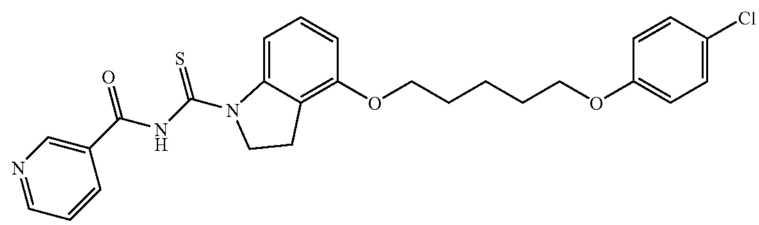 | N-{4-[5-(4-Chloro-phenoxy)-pentyloxy]-2,3-dihydro-indole-1-carbothioyl}nicotinamide |
| 18 | 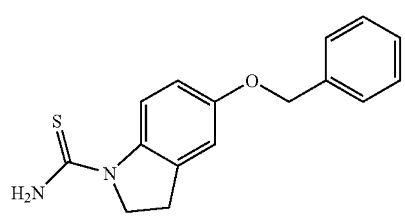 | 5-Benzyloxy-2,3-dihydro-indole-1-carbothioic acid amide |
| 19 | 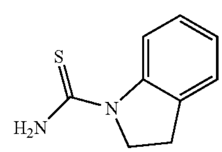 | 2,3-Dihydro-indole-1-carbothioic acid amide |
| 20 | 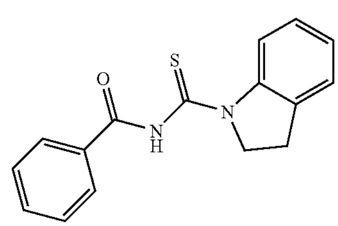 | N-(2,3-Dihydro-indole-1-carbothioyl)-benzamide |
| 21 | 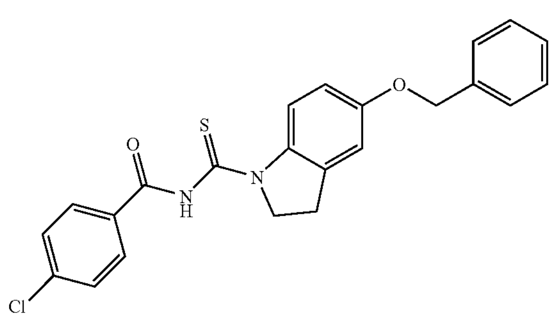 | N-(5-Benzyloxy-2,3-dihydro-indole-1-carbothioyl)-4-chloro-benzamide |

-continued

| Compound No. | Structure | Name |
|---|---|---|
| 22 | 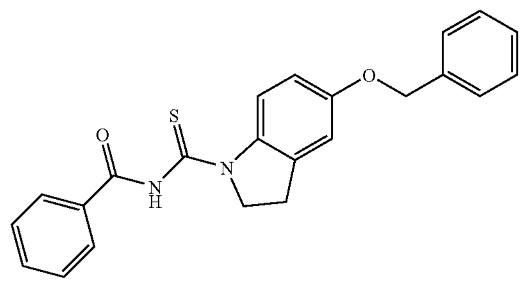 | N-(5-Benzyloxy-2,3-dihydro-indole-1-carbothioyl)benzamide |
| 23 | 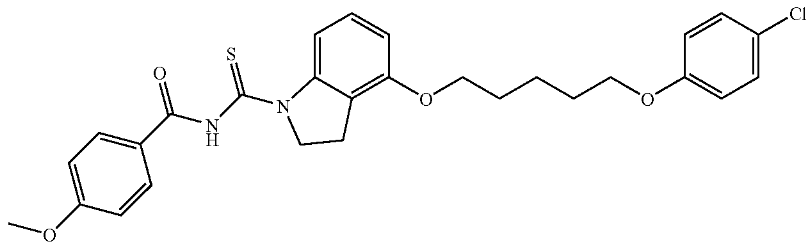 | N-{4-[5-(4-Chloro-phenoxy)-pentyloxy]-2,3-dihydro-indole-1-carbothioyl}-4-methoxy-benzamide |
| 24 | 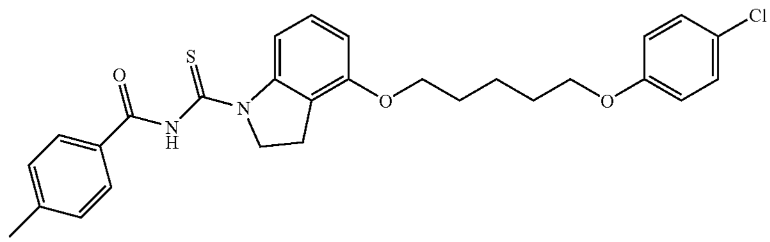 | N-{4-[5-(4-Chloro-phenoxy)-pentyloxy]-2,3-dihydro-indole-1-carbothioyl}-4-methyl-benzamide |
| 25 | 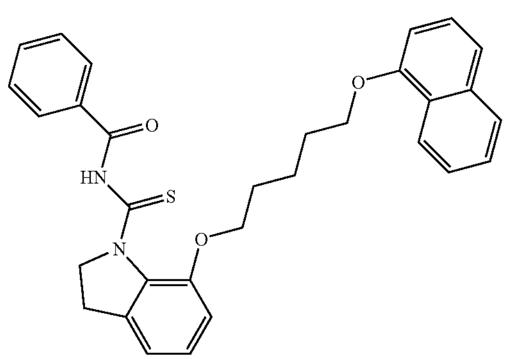 | N-{7-[5-(Naphthalen-1-yloxy)-pentyloxy]-2,3-dihydro-indole-1-carbothioyl}benzamide |
| 26 | 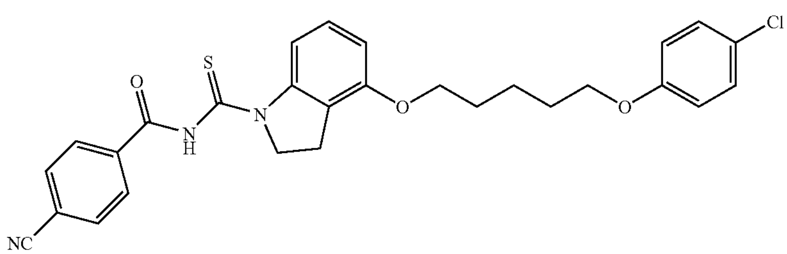 | N-{4-[5-(4-Chloro-phenoxy)-pentyloxy]-2,3-dihydro-indole-1-carbothioyl}-4-cyanobenzamide |

-continued

| Compound No. | Name |
|---|---|
| 27 | N-{4-[5-(4-Chloro-phenoxy)-pentyloxy]-2,3-dihydro-indole-1-carbothioyl}-4-nitrobenzamide |
| 28 | N-{4-[5-(4-Chloro-phenoxy)-pentyloxy]-2,3-dihydro-indole-1-carbothioyl}-3,4,5-trimethoxybenzamide |
| 29 | 4-tert-Butyl-N-{4-[5-(4-chloro-phenoxy)-pentyloxy]-2,3-dihydro-indole-1-carbothioyl}benzamide |
| 30 | Thiophene-2-carboxylic acid {4-[5-(4-chloro-phenoxy)-pentyloxy]-2,3-dihydro-indole-1-carbothioyl}amide |
| 31 | N-{4-[5-(4-Chloro-phenoxy)-pentyloxy]-2,3-dihydro-indole-1-carbothioyl}-4-trifluoromethylbenzamide |

-continued

| Compound No. | Structure | Name |
|---|---|---|
| 32 | 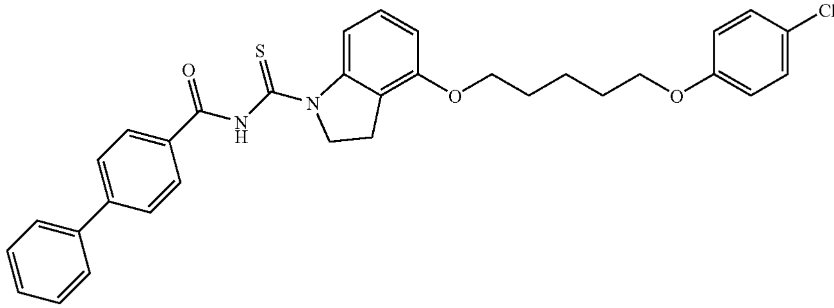 | Biphenyl-4-carboxylic acid {4-[5-(4-chloro-phenoxy)-pentyloxy]-2,3-dihydro-indole-1-carbothioyl}amide |
| 33 | 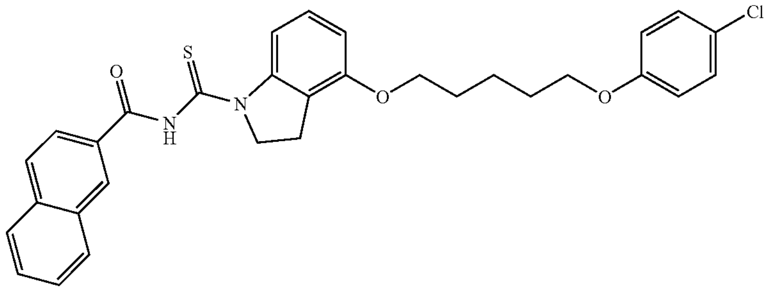 | Naphthalene-2-carboxylic acid {4-[5-(4-chloro-phenoxy)-pentyloxy]-2,3-dihydro-indole-1-carbothioyl}amide |
| 34 | 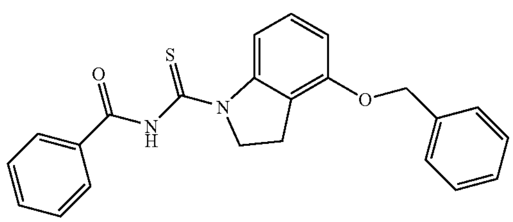 | N-(4-Benzyloxy-2,3-dihydro-indole-1-carbothioyl)benzamide |
| 35 | 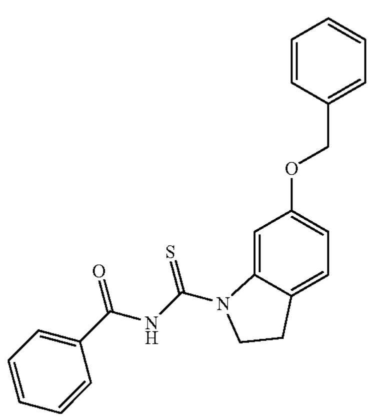 | N-(6-Benzyloxy-2,3-dihydro-indole-1-carbothioyl)benzamide |

| Compound No. | Structure | Name |
|---|---|---|
| 36 | 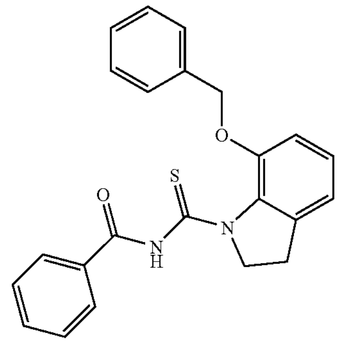 | N-(7-Benzyloxy-2,3-dihydro-indole-1-carbothioyl)benzamide |
| 37 | 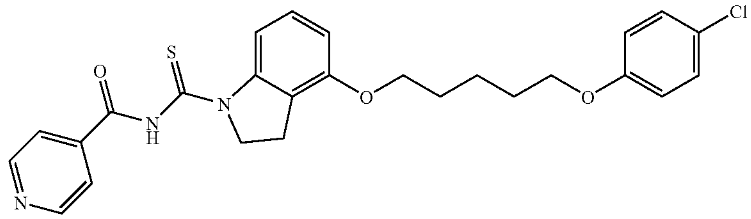 | N-{4-[5-(4-Chloro-phenoxy)-pentyloxy]-2,3-dihydro-indole-1-carbothioyl}isonicotinamide |
| 38 | 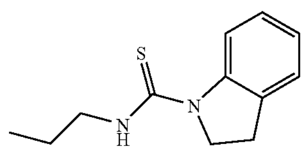 | 2,3-Dihydro-indole-1-carbothioic acid propylamide |
| 39 | 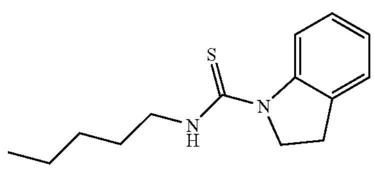 | 2,3-Dihydro-indole-1-carbothioic acid pentylamide |
| 40 | 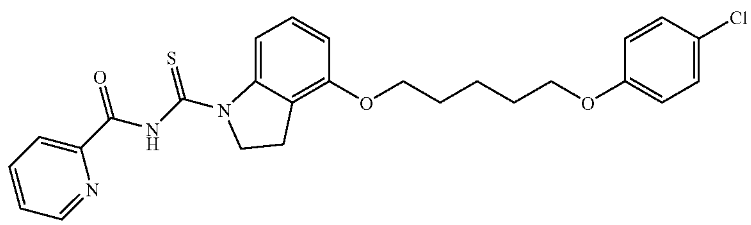 | Pyridine-2-carboxylic acid {4-[5-(4-chloro-phenoxy)-pentyloxy]-2,3-dihydro-indole-1-carbothioyl}amide |

In still another aspect, this invention relates to a method of treating HCV infection by administering to a subject infected with HCV an effective amount of the thiourea compounds described herein.

Also within the scope of this invention is a pharmaceutical composition containing one or more of the above-described thiourea compounds for use in treating a HCV infection, as well as this therapeutic use and use of the compound for the manufacture of a medicament for treating HCV infection.

The details of one or more embodiments of the invention are set forth in the description below. Other features, objects, and advantages of the invention will be apparent from the description and drawings, and from the claims.

DETAILED DESCRIPTION

The thiourea compounds described above can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-2 below show useful transformations for synthesizing the compounds of this invention.

The compounds of this invention have a partially unsaturated N-containing bicyclic moiety. This moiety can be prepared by cyclization or by reduction of an aromatic bicyclic ring. Scheme 1 below shows two exemplary reactions for making this moiety.

Scheme 1

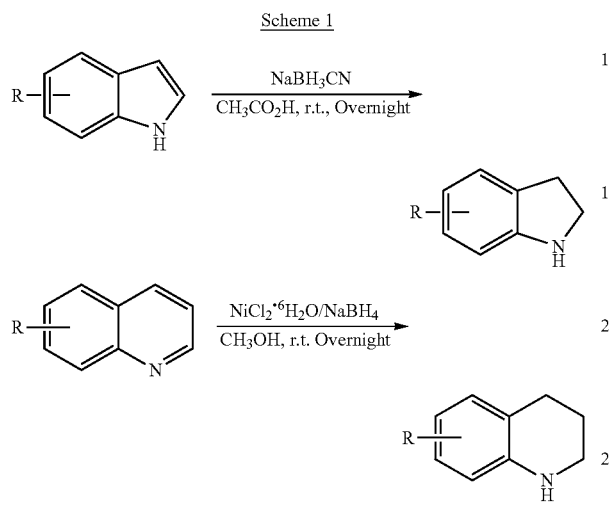

The compounds of this invention also have a thiourea moiety. This moiety can be prepared by reacting N-containing bicyclic moiety with thiocarbonyl diimidazole (TCDI) followed by treatment of amine or ammonium, or by reacting N-containing bucyclic moiety with an isothiocyanate (—NCS) compound. See Scheme 2 below.

Scheme 2

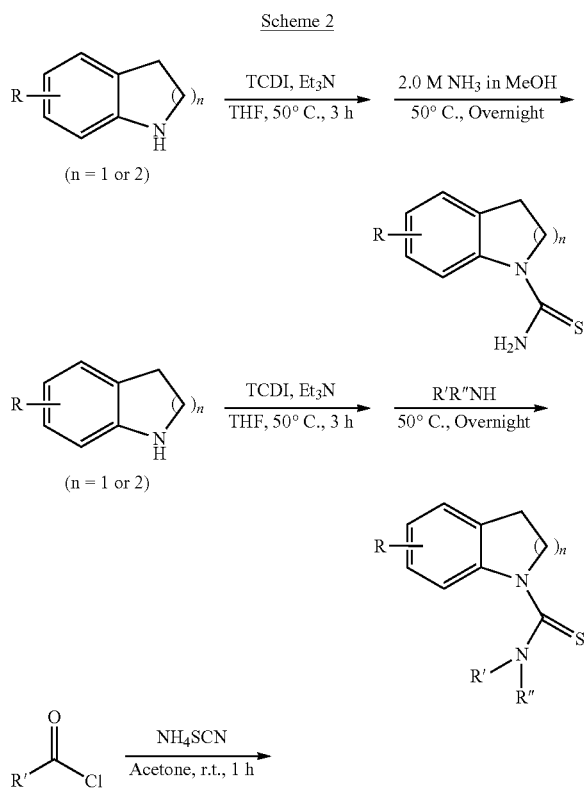

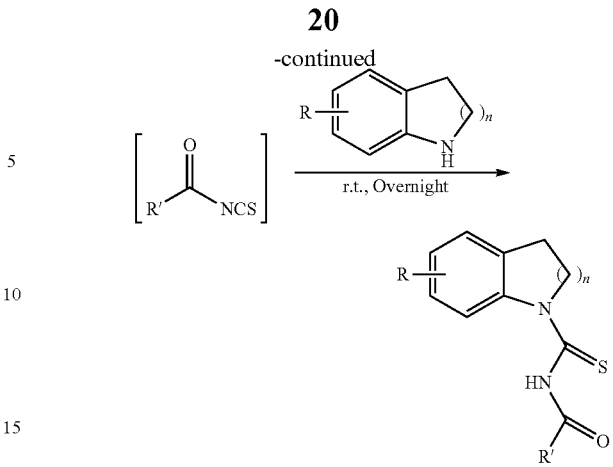

A thiourea compound thus synthesized can be further purified by flash column chromatography, high performance liquid chromatography, crystallization, or any other suitable methods.

Also within the scope of this invention are (1) a pharmaceutical composition that contains an effective amount of at least one of the thiourea compounds described above and a pharmaceutically acceptable carrier, and (2) a method for treating HCV infection by administering to a subject in need of this treatment an effective amount of such a thiourea compound.

As used herein, the term "treating" refers to administering a thiourea compound to a subject that has HCV infection, or has a symptom of HCV infection, or has a predisposition toward HCV infection, with the purpose to prevent, cure, heal, alleviate, relieve, alter, remedy, ameliorate, improve, or affect the HCV infection, the symptoms of the HCV infection, or the predisposition toward the HCV infection. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method provided in this application, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A thiourea compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the thiourea compounds, or more solubilizing agents, can be utilized as pharmaceutical carriers for delivery of the oxadiazole compounds. Examples of other carriers include colloidal silicon dioxide, magnesium stearate, sodium lauryl sulfate, and D&C Yellow #10.

Suitable in vitro assays can be used to preliminarily evaluate the efficacy of the thiourea compounds of this invention in inhibiting HCV replication. The compounds can further be examined for their efficacy in treating HCV infection. For example, a compound can be administered to an animal (e.g., a mouse model) infected with HCV and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 4-fluoro-N-{5-[5-(naphthalen-1-yloxy)-pentyloxy]-3,4-dihydro-2H-quinoline-1-carbothioyl}-benzamide (Compound 3)

To a stirred suspension of 5-hydroxyquinoline (10.0 g, 69.0 mmol) and 1,5-dibromo-pentane (23.9 g, 103.5 mmol) in N-methylpyrrolidinone (100 mL) was added potassium carbonate (14.7 g, 103.5 mmol). The resulting mixture was stirred at 90° C. for 4 h and then quenched with water (30 mL) followed by extraction with ethyl acetate (30 mL×3). The organic layers were combined, washed with brine, and then concentrated under vacuum. The residue was purified by silica gel chromatography to give 5-(5-bromo-pentyloxy)-quinoline (12.6 g, 42.8 mmol, 62%) as a white solid.

The above-obtained compound (1.06 g, 3.62 mmol) was suspended together with 1-naphthol (521 mg, 3.62 mmol) and potassium iodide (60 mg, 0.36 mmol) in N-methylpyrrolidinone (10 mL). To the suspension, potassium carbonate (0.75 g, 5.42 mmol) was added. After stirred at 90° C. for 4 h, the reaction mixture was quenched with water (30 mL) followed by extraction with ethyl acetate (30 mL×3). The organic layers were combined, washed with brine, and concentrated under vacuum. The residue was purified by silica gel chromatography to give 5-[5-(naphthalen-1-yloxy)-pentyloxy]-quinoline (1.11 g, 3.11 mmol, 86%) as a white solid.

To a solution of 5-[5-(naphthalen-1-yloxy)-pentyloxy]-quinoline (0.83 g, 2.32 mmol) in 10 mL methanol and 1 mL THF was added sodium borohydride (0.35 g, 9.29 mmol) and nickel (II) chloride hexahydrate (0.28 g, 1.16 mmol). The reaction mixture was stirred overnight at room temperature and then 20 mL saturated aqueous ammonium chloride solution was added. The solution was extracted with ethyl acetate (3×20 mL), and the combined organic phases were washed with brine, dried over $MgSO_4$, and concentrated to give a white solid. The crude product was purified by silica gel chromatography to give 5-[5-(naphthalen-1-yloxy)-pentyloxy]-1,2,3,4-tetrahydro-quinoline (335 mg, 0.93 mmol, 40%) as a white solid.

To a stirred solution of 4-fluorobenzoyl chloride (38 mg, 0.24 mmol) in acetone (2.0 mL) was added ammonium thiocyanate (51 mg, 0.66 mmol). The resulting mixture was stirred for 1 h at room temperature followed by the addition of the above-obtained tetrahydroquinoline compound (80 mg, 0.22 mmol). After stirred overnight at room temperature, the reaction mixture was quenched with excess saturated ammonium chloride (20 mL) followed by extraction with ethyl acetate (3×20 L). The organic layers were combined, washed with brine, and then concentrated under vacuum. The residue was purified by silica gel chromatography to give 4-fluoro-N-{5-[5-(naphthalen-1-yloxy)-pentyloxy]-3,4-dihydro-2H-quinoline-1-carbothioyl}-benzamide (83 mg, 0.15 mmol, 70%) as a white solid. MS (EI): m/z 543 (M+H).

Example 2

Synthesis of 5-[5-(naphthalen-1-yloxy)-pentyloxy]-3,4-dihydro-2H-quinoline-1-carbothioic acid amide (Compound 4)

To a solution of 5-[5-(naphthalen-1-yloxy)-pentyloxy]-1,2,3,4-tetrahydro-quinoline (100 mg, 0.28 mmol) and thiocarbonyl diimidazole (64 mg, 0.36 mmol) in dry THF (3 mL) was added triethylamine (30 mg, 0.3 mmol). After stirred at 50° C. for 3 h, the reaction mixture was treated with excess 2.0 M ammonia in methanol (4 mL). The stirring was continued overnight at 50° C. After removal of the solvent, the residue was purified by silica gel chromatography to give 5-[5-(naphthalen-1-yloxy)-pentyloxy]-3,4-dihydro-2H-quinoline-1-carbothioic acid amide, compound 4 (88 mg, 0.21 mmol, 75%) as a white solid. MS (EI): m/z 421 (M+H).

Example 3

Synthesis of N-{4-[5-(4-chloro-phenoxy)-pentyloxy]-2,3-dihydro-indole-1-carbothioyl}-benzamide (Compound 7)

To a stirred suspension of 4-hydroxyindole (10.0 g, 75.2 mmol) and 1,5-dibromo-pentane (26.0 g, 112.8 mmol) in N-methylpyrrolidinone (100 mL) was added potassium carbonate (16.0 g, 112.8 mmol). The resulting mixture was stirred at 90° C. for 4 hours and then quenched with water (30 mL) followed by extraction with ethyl acetate (30 mL×3). The organic layers were combined, washed with brine, and then concentrated under vacuum. The resulting residue was purified by silica gel chromotography to give 4-(5-bromo-pentyloxy)-1H-indole (14.0 g, 49.6 mmol, 66%) as a white solid.

The above-obtained compound (2.0 g, 7.1 mmol) was suspended together with p-chlorophenol (916 mg, 7.1 mmol) and potassium iodide (116 mg, 0.7 mmol) in N-methylpyrrolidinone (20 mL). To the suspension was added potassium carbonate (1.50 g, 10.7 mmol) under stirring. The resulting mixture was stirred at 90° C. for 4 hours and then quenched with water (30 mL) followed by extraction with ethyl acetate (30 mL×3). The organic layers were combined, washed with brine, and then concentrated under vacuum. The residue was purified by silica gel chromatography to give 4-[5-(4-chloro-phenoxy)-pentyloxy]-1H-indole (2.12 g, 6.4 mmol, 90%) as a white solid.

To a solution of 4-[5-(4-chloro-phenoxy)-pentyloxy]-1H-indole (1.72 g, 5.2 mmol) in 20 mL acetic acid was added sodium cyanoborohydride (2.61 g, 41.6 mmol). After stirred overnight at room temperature, the reaction mixture was treated with saturated aqueous sodium bicarbonate solution (50 mL). The solution was then extracted with ethyl acetate (3×50 mL), and the combined organic phases were washed with brine, dried over $MgSO_4$, and concentrated to give a crude product as a white solid. The crude product was purified by silica gel column chromatography to give 4-[5-(4-chloro-phenoxy)-pentyloxy]-2,3-dihydro-1H-indole (600 mg, 1.80 mmol, 35%) as a white solid.

To a stirred solution of benzoyl chloride (42 mg, 0.3 mmol) in acetone (3.0 mL) was added ammonium thiocyanate (68 mg, 0.9 mmol). The resulting mixture was stirred for 1 h at room temperature followed by addition of the indoline compound 4-[5-(4-chloro-phenoxy)-pentyloxy]-2,3-dihydro-1H-indole (100 mg, 0.3 mmol). After stirred overnight at room temperature, the reaction mixture was quenched with excess saturated ammonium chloride (30 mL) and extracted with ethyl acetate (30 mL×3). The organic layers were combined, washed with brine, and then concentrated under vacuum. The residue was purified by silica gel chromatography to give N-{4-[5-(4-chloro-phenoxy)-pentyloxy]-2,3-dihydro-indole-1-carbothioyl}-benzamide (74 mg, 0.15 mmol, 50%) as a white solid. MS (EI): m/z 495 (M+H).

Example 4

Synthesis of 4-[5-(4-chloro-phenoxy)-pentyloxy]-2,3-dihydro-indole-1-carbothioic acid amide (Compound 8)

To a solution of 4-[5-(4-chloro-phenoxy)-pentyloxy]-2,3-dihydro-1H-indole (100 mg, 0.3 mmol) and thiocarbonyl diimidazole (64 mg, 0.36 mmol) in dry THF (3 mL) was added triethylamine (30 mg, 0.3 mmol). The reaction mixture was stirred at 50° C. for 3 hours and then 2.0 M ammonia in 4 mL methanol (excess) was added. The stirring was continued overnight at 50° C. After removal of the solvent, the residue was purified by silica gel column chromatography to give 4-[5-(4-chloro-phenoxy)-pentyloxy]-2,3-dihydro-indole-1-carbothioic acid amide, compound 8 (101 mg, 0.26 mmol, 85%) as a white solid. MS (EI): m/z 391 (M+H).

Example 5

Synthesis of 4-(5-phenoxy-pentyloxy)-2,3-dihydro-indole-1-carbothioic acid amide (Compound 1)

The compound was prepared in a manner similar to that described in Example 4. EI-MS (M+1): 357.

Example 6

Synthesis of 6-(5-phenoxy-pentyloxy)-2,3-dihydro-indole-1-carbothioic acid amide (Compound 2)

The compound was prepared in a manner similar to that described in Example 4. EI-MS (M+1): 357.

Example 7

Synthesis of 4-[5-(naphthalen-1-yloxy)-pentyloxy]-2,3-dihydro-indole-1-carbothioic acid amide (Compound 5)

The compound was prepared in a manner similar to that described in Example 4. EI-MS (M+1): 407.

Example 8

Synthesis of 4-[5-(4-fluoro-phenoxy)-pentyloxy]-2,3-dihydro-indole-1-carbothioic acid amide (Compound 6)

The compound was prepared in a manner similar to that described in Example 4. EI-MS (M+1): 375.

Example 9

Synthesis of N-{4-[5-(naphthalen-1-yloxy)-pentyloxy]-2,3-dihydro-indole-1-carbothioyl}-benzamide (Compound 9)

The compound was prepared in a manner similar to that described in Example 3. EI-MS (M+1): 511.

Example 10

Synthesis of N-{4-[5-(4-fluoro-phenoxy)-pentyloxy]-2,3-dihydro-indole-1-carbothioyl}-benzamide (Compound 10)

The compound was prepared in a manner similar to that described in Example 3. EI-MS (M+1): 479.

Example 11

Synthesis of 4-chloro-N-{4-[5-(4-chloro-phenoxy)-pentyloxy]-2,3-dihydro-indole-1-carbothioyl}-benzamide (Compound 11)

The compound was prepared in a manner similar to that described in Example 3. EI-MS (M+1): 529.

Example 12

Synthesis of furan-2-carboxylic acid {4-[5-(4-chloro-phenoxy)-pentyloxy]-2,3-dihydro-indole-1-carbothioyl}-amide (Compound 12)

The compound was prepared in a manner similar to that described in Example 3. EI-MS (M+1): 485.

Example 13

Synthesis of 6-[5-(naphthalen-1-yloxy)-pentyloxy]-2,3-dihydro-indole-1-carbothioic acid amide (Compound 13)

The compound was prepared in a manner similar to that described in Example 4. EI-MS (M+1): 511.

Example 14

Synthesis of N-{6-[5-(naphthalen-1-yloxy)-pentyloxy]-2,3-dihydro-indole-1-carbothioyl}-benzamide (Compound 14)

The compound was prepared in a manner similar to that described in Example 3. EI-MS (M+1): 511.

Example 15

Synthesis of 5-[5-(naphthalen-1-yloxy)-pentyloxy]-2,3-dihydro-indole-1-carbothioic acid amide (Compound 15)

The compound was prepared in a manner similar to that described in Example 4. EI-MS (M+1): 511.

Example 16

Synthesis of N-{5-[5-(naphthalen-1-yloxy)-pentyloxy]-2,3-dihydro-indole-1-carbothioyl}-benzamide (Compound 16)

The compound was prepared in a manner similar to that described in Example 3. EI-MS (M+1): 511.

Example 17

Synthesis of N-{4-[5-(4-chloro-phenoxy)-pentyloxy]-2,3-dihydro-indole-1-carbothioyl}-nicotinamide (Compound 17)

The compound was prepared in a manner similar to that described in Example 3. EI-MS (M+1): 496.

Example 18

Synthesis of 5-benzyloxy-2,3-dihydro-indole-1-carbothioic acid amide (Compound 18)

The compound was prepared in a manner similar to that described in Example 4. EI-MS (M+1): 285.

Example 19

Synthesis of 2,3-dihydro-indole-1-carbothioic acid amide (Compound 19)

The compound was prepared in a manner similar to that described in Example 4. EI-MS (M+1): 179.

Example 20

Synthesis of N-(2,3-dihydro-indole-1-carbothioyl)-benzamide (Compound 20)

The compound was prepared in a manner similar to that described in Example 3. EI-MS (M+1): 283.

Example 21

Synthesis of N-(5-benzyloxy-2,3-dihydro-indole-1-carbothioyl)-4-chloro-benzamide (Compound 21)

The compound was prepared in a manner similar to that described in Example 3. EI-MS (M+1): 423.

Example 22

Synthesis of N-(5-benzyloxy-2,3-dihydro-indole-1-carbothioyl)-benzamide (Compound 22)

The compound was prepared in a manner similar to that described in Example 3. EI-MS (M+1): 389.

Example 23

Synthesis of N-{4-[5-(4-chloro-phenoxy)-pentyloxy]-2,3-dihydro-indole-1-carbothioyl}-4-methoxy-benzamide (Compound 23)

The compound was prepared in a manner similar to that described in Example 3. EI-MS (M+1): 525.

Example 24

Synthesis of N-{4-[5-(4-chloro-phenoxy)-pentyloxy]-2,3-dihydro-indole-1-carbothioyl}-4-methyl-benzamide (Compound 24)

The compound was prepared in a manner similar to that described in Example 3. EI-MS (M+1): 509.

Example 25

Synthesis of N-{7-[5-(naphthalen-1-yloxy)-pentyloxy]-2,3-dihydro-indole-1-carbothioyl}-benzamide (Compound 25)

The compound was prepared in a manner similar to that described in Example 3. EI-MS (M+1): 511.

Example 26

Synthesis of N-{4-[5-(4-chloro-phenoxy)-pentyloxy]-2,3-dihydro-indole-1-carbothioyl}-4-cyano-benzamide (Compound 26)

The compound was prepared in a manner similar to that described in Example 3. EI-MS (M+1): 520.

Example 27

Synthesis of N-{4-[5-(4-chloro-phenoxy)-pentyloxy]-2,3-dihydro-indole-1-carbothioyl}-4-nitro-benzamide (Compound 27)

The compound was prepared in a manner similar to that described in Example 3. EI-MS (M+1): 540.

Example 28

Synthesis of N-{4-[5-(4-chloro-phenoxy)-pentyloxy]-2,3-dihydro-indole-1-carbothioyl}-3,4,5-tri-methoxy-benzamide (Compound 28)

The compound was prepared in a manner similar to that described in Example 3. EI-MS (M+1): 585.

Example 29

Synthesis of 4-tert-butyl-N-{4-[5-(4-chloro-phenoxy)-pentyloxy]-2,3-dihydro-indole-1-carbothioyl}-benzamide (Compound 29)

The compound was prepared in a manner similar to that described in Example 3. EI-MS (M+1): 551.

Example 30

Synthesis of thiophene-2-carboxylic acid {4-[5-(4-chloro-phenoxy)-pentyloxy]-2,3-dihydro-indole-1-carbothioyl}amide (Compound 30)

The compound was prepared in a manner similar to that described in Example 3. EI-MS (M+1): 501.

Example 31

Synthesis of N-{4-[5-(4-Chloro-phenoxy)-pentyloxy]-2,3-dihydro-indole-1-carbothioyl}-4-trifluoromethyl-benzamide (Compound 31)

The compound was prepared in a manner similar to that described in Example 3. EI-MS (M+1): 563.

Example 32

Synthesis of biphenyl-4-carboxylic acid {4-[5-(4-chloro-phenoxy)-pentyloxy]-2,3-dihydro-indole-1-carbothioyl}amide (Compound 32)

The compound was prepared in a manner similar to that described in Example 3. EI-MS (M+1): 571.

Example 33

Synthesis of naphthalene-2-carboxylic acid {4-[5-(4-chloro-phenoxy)-pentyloxy]-2,3-dihydro-indole-1-carbothioyl}amide (Compound 33)

The compound was prepared in a manner similar to that described in Example 3. EI-MS (M+1): 545.

Example 34

Synthesis of N-(4-nenzyloxy-2,3-dihydro-indole-1-carbothioyl)-benzamide (Compound 34)

The compound was prepared in a manner similar to that described in Example 3. EI-MS (M+1): 389.

Example 35

Synthesis of N-(6-benzyloxy-2,3-dihydro-indole-1-carbothioyl)-benzamide (Compound 35)

The compound was prepared in a manner similar to that described in Example 3. EI-MS (M+1): 389.

Example 36

Synthesis of N-(7-benzyloxy-2,3-dihydro-indole-1-carbothioyl)-benzamide (Compound 36)

The compound was prepared in a manner similar to that described in Example 3. EI-MS (M+1): 389.

Example 37

Synthesis of N-{4-[5-(4-chloro-phenoxy)-pentyloxy]-2,3-dihydro-indole-1-carbothioyl}isonicotinamide (Compound 37)

The compound was prepared in a manner similar to that described in Example 3. EI-MS (M+1): 496.

Example 38

Synthesis of 2,3-dihydro-indole-1-carbothioic acid propylamide (Compound 38)

The compound was prepared in a manner similar to that described in Example 4. EI-MS (M+1): 221.

Example 39

Synthesis of 2,3-Dihydro-indole-1-carbothioic acid pentylamide (Compound 39)

The compound was prepared in a manner similar to that described in Example 4. EI-MS (M+1): 249.

Example 40

Synthesis of pyridine-2-carboxylic acid {4-[5-(4-chloro-phenoxy)-pentyloxy]-2,3-dihydro-indole-1-carbothioyl}amide (Compound 40)

The compound was prepared in a manner similar to that described in Example 3. EI-MS (M+1): 496.

Example 41

Inhibiting HCV Replication

Ava5-EG (Δ4AB)SEAP, a reporter-based cell line, was used for testing whether a compound inhibited HCV replication, following the method described in Lee et al., Anal. Biochem., 316:162-70 (2003) and Lee et al., J. Virol Methods, 116:27-33.

The Ava5-EG (Δ4AB)SEAP cells were cultured in a medium containing 500 μg/ml G418 and 10 μg/ml blasticidin in a 5% $CO_2$ incubator. Before treated with a test compound, the cells were seeded in a 96-well plate at a density of $5\times10^3$ cells per well and incubated for 24 hours. The cells were then treated with the compound at different concentrations. After 48 hours, the culture medium in each well was replaced with a fresh medium containing the compound at the same concentration. By doing so, secreted alkaline phosphatase (SEAP), if any accumulated in the culture medium, were removed. The cells were cultured for additional 24 hours. The culture medium was then collected and analyzed for SEAP activity using Phospha-Light assay kit (Tropix, Foster, Calif., USA).

Compounds 1-25 were tested in this assay. Most of them had low $EC_{50}$ values indicating that they were effective in inhibiting HCV replication. Unexpectedly, some compounds had $EC_{50}$ values lower than 2 μM.

Example 42

Cytotoxicity Assay

Cell viability after compound treatment was determined by the MTS assay described in Cory et al., Cancer Commun., 3:207-12 (1991). Briefly, a reagent solution was added to cells cultured in a 96-well plate (100 μl/well). This reagent contained phenol red-free DMEM, MTS (tetrazolium compound [3-(4,5-dimethylthiozol-2-yl)-5-)3-carboxymethoxyphenyl)-2-(4-sulfohenyl)-2H-tetrazolium, inner salt] purchased from Promega (Madison, Wis.) and PMS (phenazine methosulfate) purchased from Sigma (St. Louis, Mo.) at a ratio of 80:20:1, respectively. The treated cells were incubated for 1-4 hours at 37° C. in a 5% $CO_2$ incubator and the absorbance at 490 nm in each well was detected.

Compounds 1-25 were tested in this assay. Most of them had high $CC_{50}$ values which are indicative of low cytotoxicity. Indeed, some of them had $CC_{50}$ values higher than 50 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to thiourea compounds described above also can be made, screened for the above-described activities and used to practice this invention. Thus, other embodiments are also within the claims.

What is claimed is:

1. A compound of formula (I):

$$R_1-(X)_x-(CH_2)_m-(Y)_y-(CH_2)_n-(Z)_z- \text{[heterocyclic core with U, V, T, W, N, S, } R_2, R_3\text{]}_p \quad (I)$$

wherein each of $R_1$ and $R_2$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl or C(O)R', in which R' is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl;

$R_3$ is C(O)R', in which R' is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl;

each of X, Y, and Z, independently, is O, N($R_a$), S, $C_1$-$C_{10}$ alkylene, $C_2$-$C_{10}$ alkenylene, $C_2$-$C_{10}$ alkynylene, $C_3$-$C_{20}$ cycloalkylene, $C_3$-$C_{20}$ heterocycloalkylene, arylene, heteroarylene, —C(O)—, —C(O)O—, —C(O)$NR_a$—, —$NR_a$C(O)$NR_b$—, —$NR_a$C(S)$NR_b$—, —$NR_a$C(O)O—, —$SO_2$—, or —$SO_2NR_a$—, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl;

each of U, V, T, and W, independently, is CR', in which R' is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, O, or N($R_aR_b$), in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl;

$$R_1-(X)_x-(CH_2)_m-(Y)_y-(CH_2)_n-(Z)_z$$

is attached to U, V, or T;

each of m and n is 0, 1, 2, 3, 4, 5, 6, or 7;

p is 1; and each of x, y, and z, independently, is 0 or 1.

2. The compound of claim 1, wherein $R_1$ is aryl or heteroaryl.

3. The compound of claim 2 wherein x is 1, y is 0, and z is 1.

4. The compound of claim 3, wherein X is O and Z is O.

5. The compound of claim 2, wherein x is 0, y is 0, and z is 1.

6. The compound of claim 5, wherein Z is O.

7. The compound of claim 2, wherein x is 0, y is 0, and z is 0.

8. The compound of claim 7, wherein m is 0 and n is 0.

9. The compound of claim 1, wherein the compound is selected from the group consisting of the compounds shown in the following table:

| Compound No. | Structure |
|---|---|
| 7 | 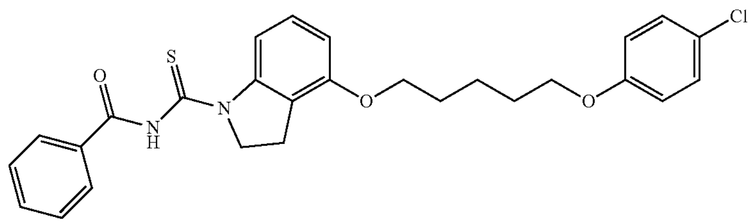 |
| 9 | 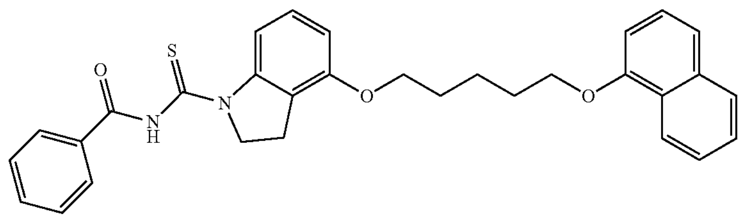 |
| 10 | 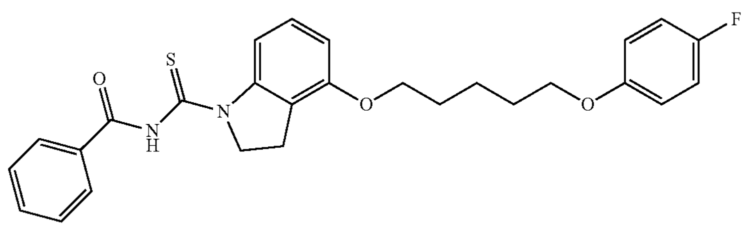 |
| 11 | 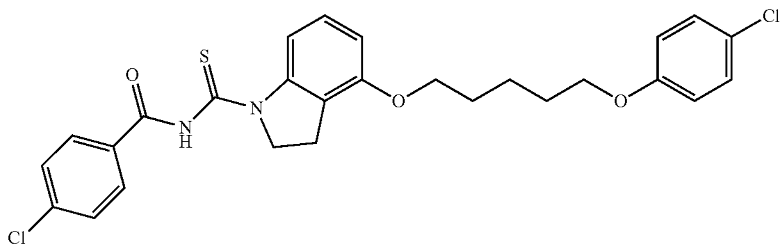 |
| 12 | 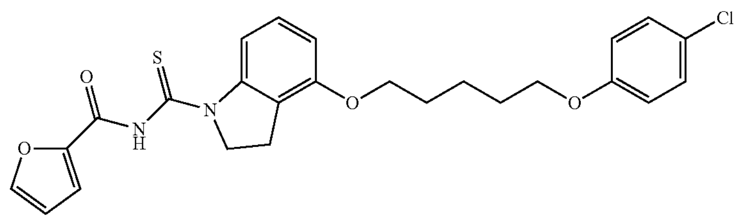 |
| 14 | 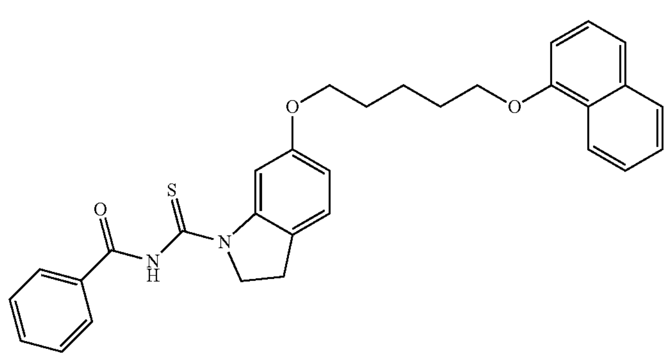 |

-continued
| Compound No. | Structure |
|---|---|
| 16 | 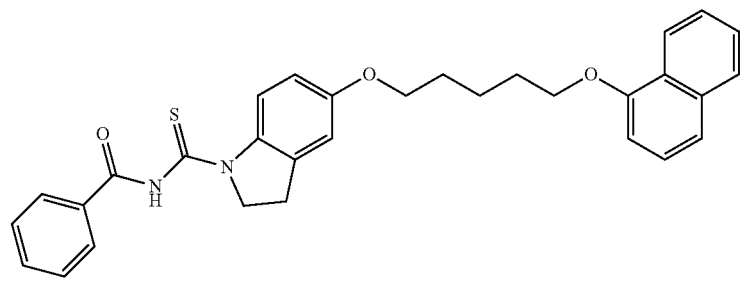 |
| 17 | 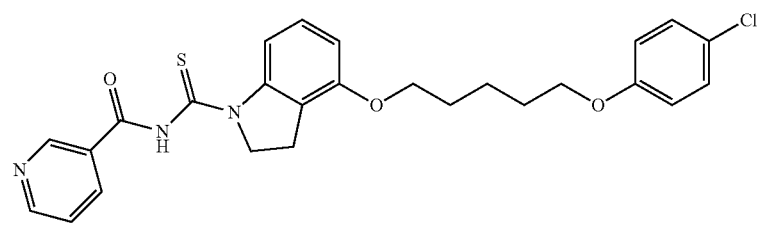 |
| 23 | 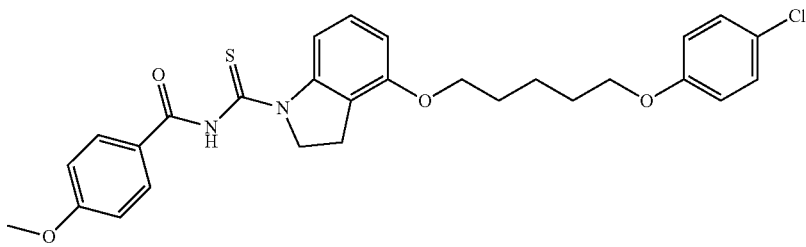 |
| 24 | 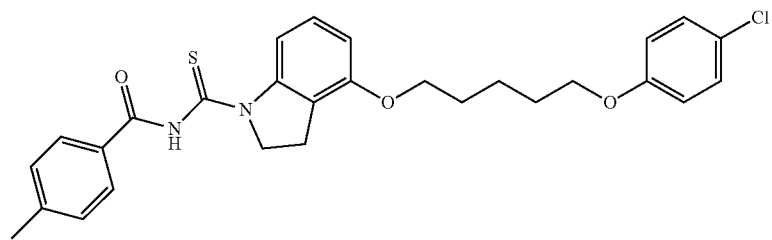 |
| 25 | 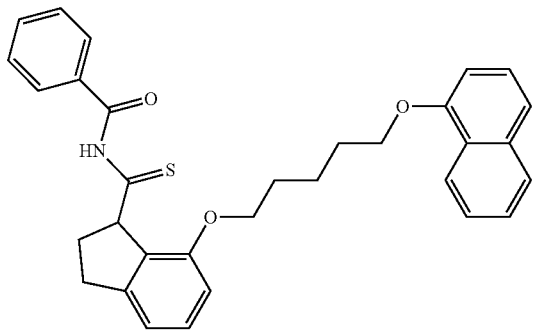 |
| 26 | 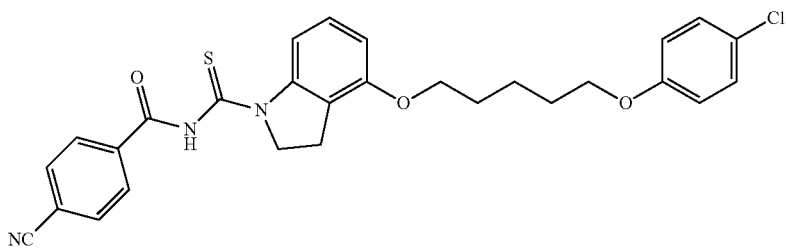 |

-continued
| Compound No. | Structure |
|---|---|
| 27 | 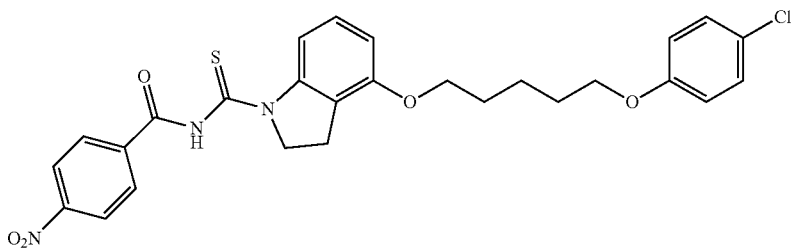 |
| 28 | 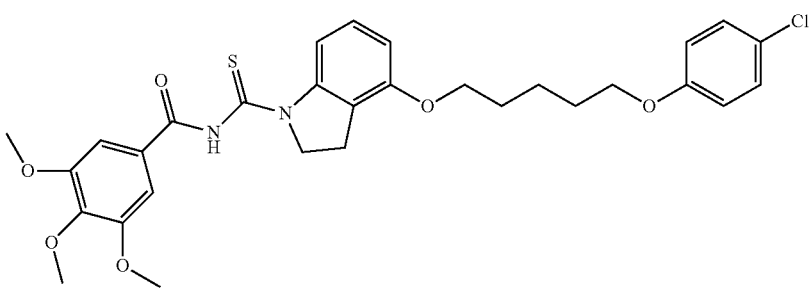 |
| 29 | 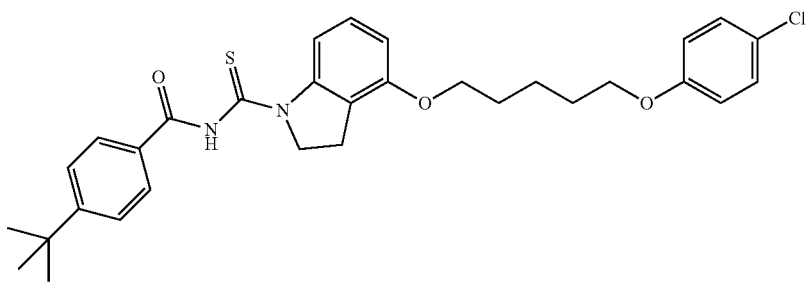 |
| 30 | 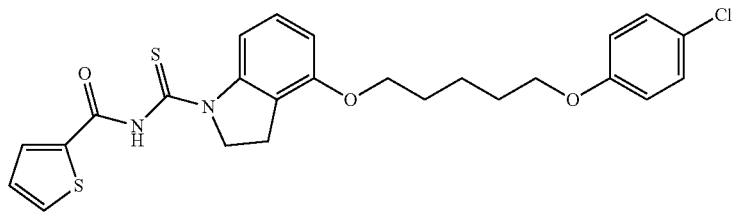 |
| 31 | 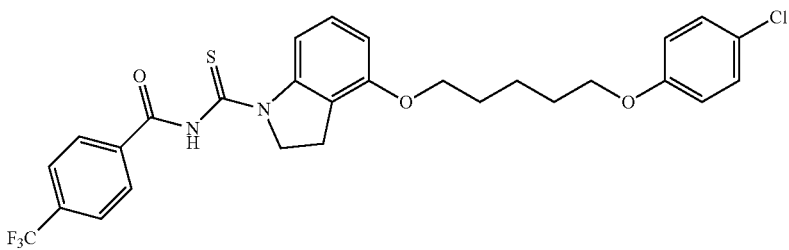 |

-continued

| Compound No. | Structure |
|---|---|
| 32 | 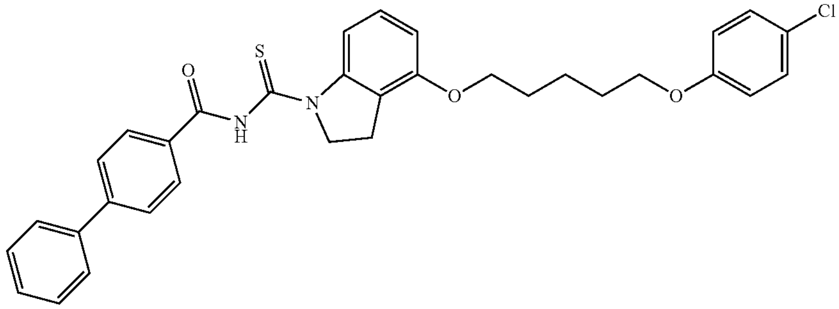 |
| 33 | 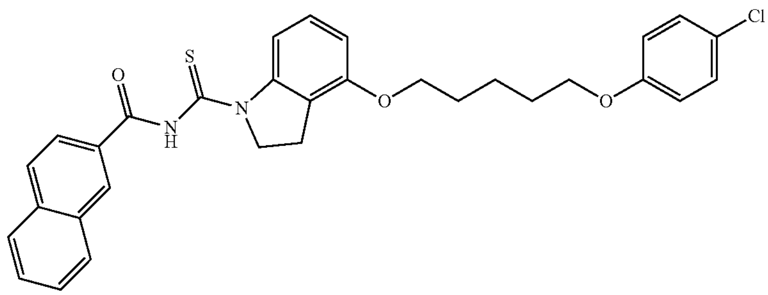 |
| 37 | 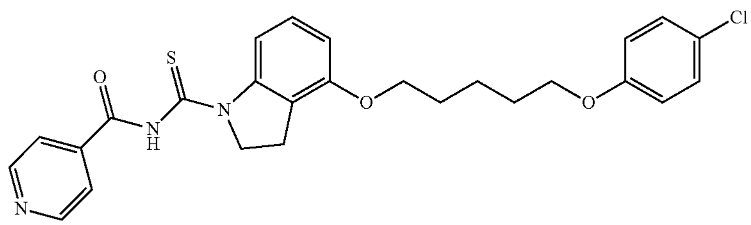 |
| 40 | | and

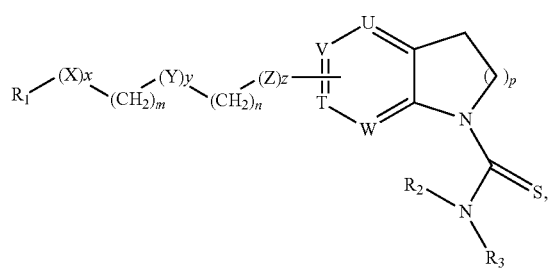

10. A compound of formula (I):

(I)

wherein

R₁ is aryl or heteroaryl;

R$_2$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ hetero-cycloalkyl, $C_3$-$C_{20}$ heterocycloalkenyl, aryl, or heteroaryl;

R$_3$ is H;

X is O and Z is O;

Y is O, N(R$_a$), S, $C_1$-$C_{10}$ alkylene, $C_2$-$C_{10}$ alkenylene, $C_2$-$C_{10}$ alkynylene, $C_3$-$C_{20}$ cycloalkylene, $C_3$-$C_{20}$ heterocycloalkylene, arylene, heteroarylene, —C(O)—, —C(O)O—, —C(O)NR$_a$—, —NR$_a$C(O)NR$_b$—, —NR$_a$C(S)NR$_b$—, —NR$_a$C(O)O—, —SO$_2$—, or —SO$_2$NR$_a$—, in which each of R$_a$ and R$_b$, independently, is H, $C_1$-$C_{10}$ alkyl, $C_3$-$C_{20}$ cycloalkyl, $C_1$-$C_{20}$ heterocycloalkyl, aryl, or heteroaryl;

each of U, V, T, and W, independently, is CR', in which R' is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, O, or N(R$_a$R$_b$), in which each of R$_a$ and R$_b$, independently, is H, $C_1$-$C_{10}$ alkyl, $C_3$-$C_{20}$ cycloalkyl, $C_3$-$C_{20}$ heterocycloalkyl, aryl, or heteroaryl;

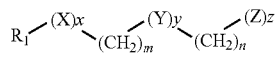
is attached to U or V;
each of m and n is 0, 1, 2, 3, 4, 5, 6, or 7;
p is 1;
each of x and z is 1; and
y is 0.
11. The compound of claim 10, wherein the compound is selected from the group consisting of the compounds shown in the following table:
| Compound No. | Structure |
| --- | --- |
| 1 | 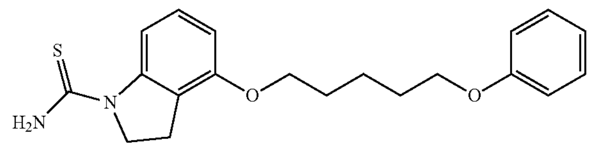 |
| 2 | 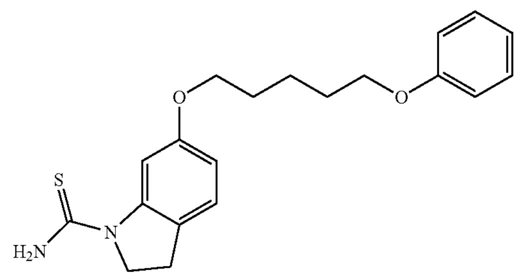 |
| 5 | 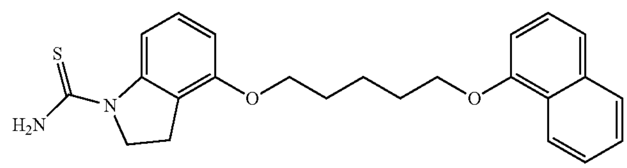 |
| 6 | 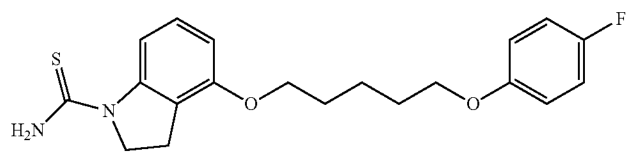 |
| 8 | 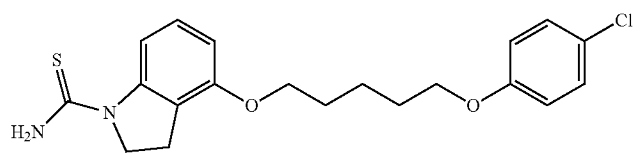 |
| 13 | 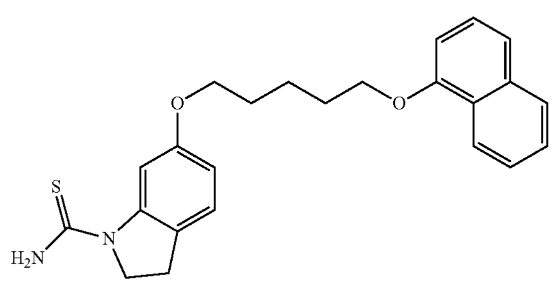 |
and

| Compound No. | Structure |
|---|---|
| 15 | 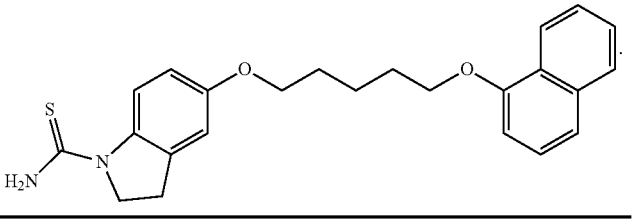 |
12. A pharmaceutical composition, comprising a compound of claim 1 and a pharmaceutically acceptable carrier.
13. A pharmaceutical composition, comprising a compound of claim 10 and a pharmaceutical acceptable carrier.
\* \* \* \* \*